United States Patent [19]
Castellani

[11] Patent Number: 5,540,766
[45] Date of Patent: Jul. 30, 1996

[54] THERMOPLASTIC COMPOSITION FOR ROOT CANAL FILLING

[76] Inventor: Nahor O. Castellani, Rua Silvia 146 #62, Sao Paulo, Brazil, 01331-010

[21] Appl. No.: 419,444

[22] Filed: Apr. 10, 1995

[51] Int. Cl.⁶ .................................................. A61C 13/38
[52] U.S. Cl. ........................ 106/35; 433/228.1; 433/224
[58] Field of Search .......................... 106/35; 433/212.1, 433/228.1, 224

[56] References Cited

U.S. PATENT DOCUMENTS

| | | | |
|---|---|---|---|
| 6,110 | 2/1849 | Hill et al. | 106/35 |
| 2,599,445 | 6/1952 | Gordon | 106/35 |
| 3,047,408 | 7/1962 | Dougherty | 106/35 |
| 4,240,832 | 12/1980 | Jandourek | 106/35 |
| 4,657,592 | 4/1987 | Takubo | 106/35 |
| 4,698,376 | 10/1987 | Asmussen et al. | 523/115 |
| 4,740,245 | 4/1988 | Futami et al. | 106/35 |
| 5,141,560 | 8/1992 | Combe et al. | 106/35 |
| 5,238,491 | 8/1993 | Sugihara et al. | 106/35 |

FOREIGN PATENT DOCUMENTS

| | | |
|---|---|---|
| 137309 | 11/1902 | Germany . |
| 958148 | 1/1957 | Germany . |
| 1030507 | 2/1986 | Japan . |
| 1085305 | 4/1986 | Japan . |
| 13084 | of 1903 | United Kingdom . |
| 2108131 | 5/1983 | United Kingdom . |

*Primary Examiner*—Melissa Bonner
*Attorney, Agent, or Firm*—Richard C. Litman

[57] ABSTRACT

Thermoplastic compositions for cones for filling root canals include guttapercha in association with calcium hydroxide. This association provides the advantages of both guttapercha and calcium hydroxide in cones, simplifying endodontic treatment by preventing a need for dressing or apical tampons. The cones provide a continuous source of calcium hydroxide, regardless of the type of cement used with the cones. Low permeability of the cones ensures that release of calcium hydroxide is slow. Additional ingredients provide rigidity, radio-opacity and coloring. The additional ingredients include zinc oxide, aluminum oxide, barium sulfate, kaolin, and colorant. Methods for making the dental cones are also provided.

13 Claims, 1 Drawing Sheet

---

Mixing Calcium Hydroxide, Guttapercha, Barium Sulfate, Aluminum Oxide, Kaolin & Zinc Oxide In Cylinder Mixer, Forming A Paste

↓

Laminating The Paste

↓

Wiredrawing Laminated Paste In A Cylinder Wiredrawer, Forming Sheets Of Composition

↓

Cutting Sheets Into Filaments

↓

Plastifying The Filaments

↓

Rolling The Filaments Into A Predetermined Length & Conical Shape Over A Planar Surface Using Plastic Plate

THERMOPLASTIC COMPOSITION FOR ROOT CANAL FILLING

BACKGROUND OF THE INVENTION

1. Field of the Invention

The present invention relates to a new type of thermoplastic cone for root canal filling, having calcium hydroxide as an active ingredient.

2. Description of the Prior Art

An important and frequently performed dental procedure is the filling of root canals of teeth. Typically, such root canals are filled with thermoplastic cones or "points," which are attached with dental cement.

Voids between cones placed in root canals have previously been an inevitable consequence of unevenness in the canal walls and differences in diameter between canals and cones. These voids, left untreated, allow entry of oral fluids into the filled root canal, with a concomitant increased likelihood of failure of the root canal filling. In fact, it is estimated that nearly 60% of failures in endodontic treatments stem from incomplete filling of such voids in root canals.

Because of the exceptional importance of completely filling a root canal, many attempts have been made to assure complete filling. Some of these attempts have been directed to filling technique, and others to the intra-canal medication used during the dental procedure. Still other attempts have been directed to the type of filling material used. Moreover, it is currently standard practice to use dental cement, in addition to the cones, in order to complete the filling. All of these attempts fail, in one way or another, to provide a simple, reproducible, inexpensive, and foolproof solution to the serious problem of incompletely filled root canals, and consequent apical leakage.

U.S. Pat. No. 3,047,408, issued on Jul. 31, 1962, to Emery W. Dougherty describes various dental cement compositions which include calcium hydroxide with zinc oxide, colorants, and various substituted phenols. This patent does not suggest the use of guttapercha and the compositions of this patent are permeable to water.

U.S. Pat. No. 4,240,838, issued on Dec. 23, 1980, to Emil Jandourek suggests that a two paste composition, which includes calcium hydroxide and zinc oxide in a base paste and resin, silica, and pigments in a catalyst paste, may be used to facilitate healing of dental pulp and formation of secondary dentine in dental cavities and linings. This patent does not show the use of guttapercha, and does not indicate the ratios provided by the present invention.

U.S. Pat. No. 4,698,376, issued on Oct. 6, 1987, to Erik Asmussen et al., describes a coating to improve bonding between polymeric materials and collagen-containing materials. This patent does not show the use of guttapercha, rigidifiers or radio-opaque materials, and does not indicate the ratios provided by the present invention.

U.S. Pat. No. 4,740,245, issued on Apr. 26, 1988, to Shunichi Futami et al, describes a composition which includes 12% guttapercha, 8% calcium hydroxide, 70% calcium silicate, 8% paraffin wax, and 2% beeswax, all by weight. This reference additionally shows a guttapercha/zinc oxide composition. Also suggested is the use of synthetic analogs of guttapercha, including trans-1,4-polyisoprene. Additional compounds which may be used with these analogs or components, including calcium hydroxide, are discussed. This patent does not indicate the ratios provided by the present invention, and calcium hydroxide in this patent is used as an inert filler ingredient, rather than as an active ingredient.

U.S. Pat. No. 5,141,560, issued on Aug. 25, 1992, to Combe et al., describes dental cement compositions which may include calcium hydroxide and zinc oxide. This patent does not show the use of guttapercha or rigidifiers, and does not indicate the ratios provided by the present invention.

U.S. Pat. No. 5,238,491, issued on Aug. 2, 1993, to Fumihito Sugihara et al., describes a hardening material comprising calcium phosphate and an acidic hardener. This patent does not show the use of guttapercha, rigidifiers or radio-opaque materials, and does not indicate the ratios provided by the present invention.

British Patent 13,084, issued on Jan. 29, 1903, to Arthur Masur, shows the incorporation of guttapercha into various conventional dental cements. These dental cements include zinc oxide, aluminum oxide, and alkalies. This patent does not indicate the ratios provided by the present invention.

United Kingdom Patent 2 108 131, published on May 11, 1981, invented by Michael Braden, describes a dental cement having zinc oxide and calcium hydroxide, but not guttapercha. This patent does not indicate the ratios provided by the present invention.

Japanese Patent 1030507, issued on Jul. 20, 1984, to Kyocera Corp., suggests a binder for root canal filling that has fifteen to twenty percent calcium hydroxide and an X-ray contrast medium. This patent does not show the use of guttapercha or rigidifiers, and does not indicate the ratios provided by the present invention.

Japanese Patent 1085305, issued on Apr. 30, 1986, to M. Takubo, suggests that a root canal filler comprising calcium hydroxide or calcium oxide, bees wax, and a triglyceride is compatible with guttapercha. This patent does not show the use of rigidifiers or radio-opaque materials, and does not indicate the ratios provided by the present invention.

German patent 137,309, issued on Nov. 12, 1902, to Arthur Masur, suggests a composition that is thirty percent guttapercha and seventy percent zinc. This patent does not show the use of calcium hydroxide, and does not indicate the ratios provided by the present invention.

German Patent 958,148 to Bernard discusses root canal filling compositions which include alcohol or glycerol, zinc oxide, and alkaline earth oxides which upon hydration form calcium hydroxide. This patent does not show the use of guttapercha, and does not indicate the ratios provided by the present invention.

The above-cited patents are incorporated herein by reference. None of the above inventions and patents, taken either singly or in combination, is seen to describe the instant invention as claimed.

SUMMARY OF THE INVENTION

By the present invention, compositions for making cones or "points" for filling dental root canals are provided. These compositions include guttapercha in combination with calcium hydroxide, as well as various additional, enhancing additives. The combination of guttapercha with calcium hydroxide allows complete binding with the dentine, without the necessity for a temporary filling or apical tampon. Additional ingredients which may be employed include zinc oxide, aluminum oxide, kaolin, and colorant.

Accordingly, it is a principal object of the invention to provide filling compositions for use in dental procedures that obviate a need for dressing and apical tampons.

An additional object of the invention is to maintain a continuous source of calcium hydroxide inside a filled root canal.

It is another object of the invention to provide a composition that ensures complete binding between the composition and tooth material to which the composition is applied.

It is a further object of the invention to provide a root canal filling composition with which various enhancing additives may be combined, such as additives that increase rigidity and radio-opacity, without causing loss of the desirable characteristics of the filling composition prior to combination with such additives.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
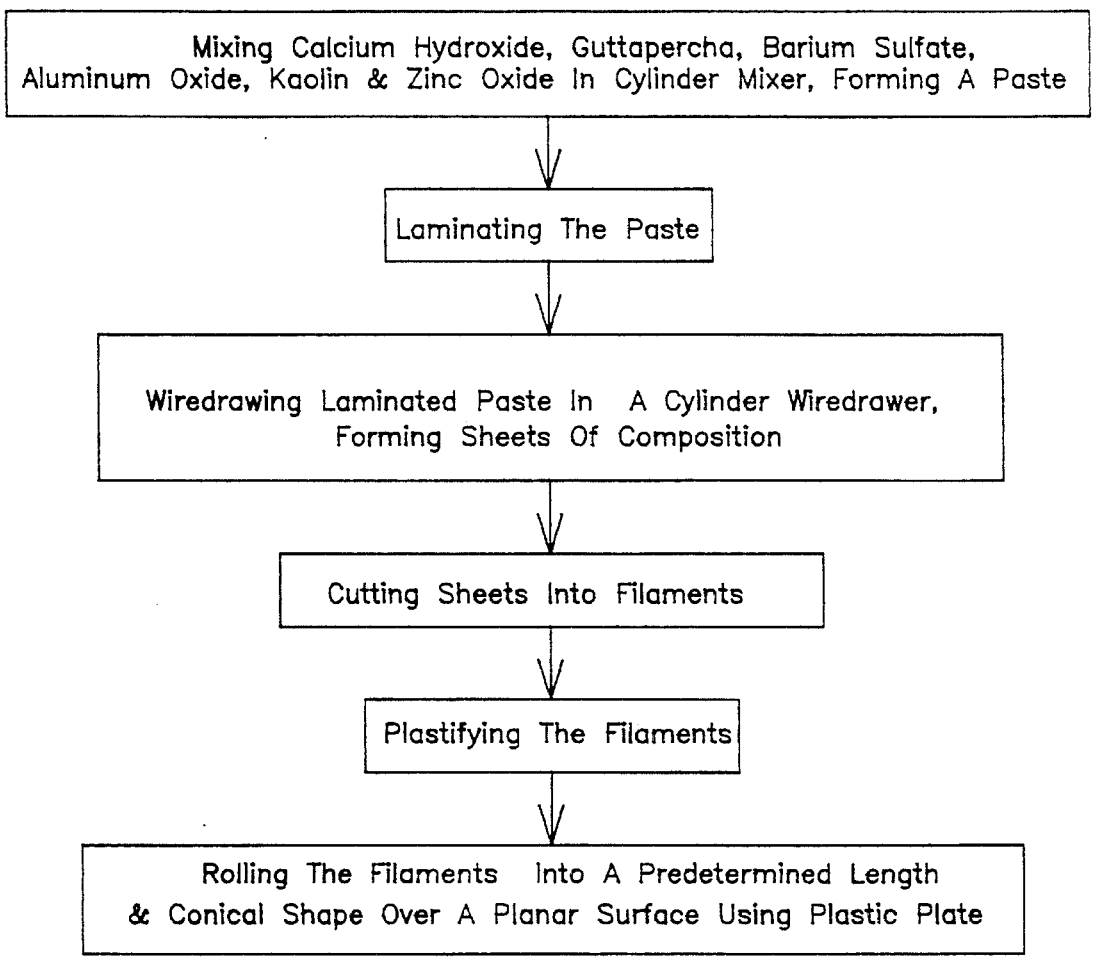
FIG. 1 is a flow chart showing a method of using the dental composition of the present invention.
Figure 2:
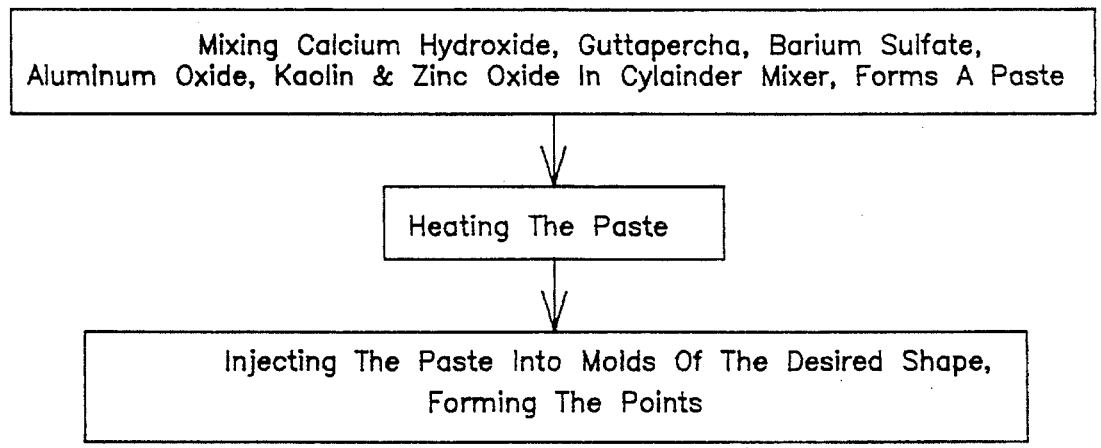
FIG. 2 is a flow chart showing another method of using the dental composition of the present invention.

Among all the substances used for root canal filling material, guttapercha in thermoplastic cones and calcium hydroxide in endodontic cement, are most preferred. According to modern practice, guttapercha cones are comprised primarily by guttapercha, as a binding agent, and inert substances such as zinc oxide and barium sulphate. Thus, there are typically no active ingredients in the guttapercha cones. The present invention, in contrast, has calcium hydroxide as an active ingredient.

Calcium hydroxide, when applied to reamed dentine, has the advantages that the calcium hydroxide: (1) protects pulp tissue against acid attack resulting from other dental preparations that include inorganic or organic acids; (2) stimulates formation of protective secondary dentine wherever applied to dental pulp; (3) controls root inflammatory reabsorption and exudates, and is thus useful in cases of fractured roots; and (4) seals root canals by expanding the filling, by preventing entry of oral fluids into the filled root canal, and by decreasing dentine permeability.

Guttapercha, as obtained naturally, comprises the purified exudate of various trees of the genus Palaguium, Sapotaceae. A synthetic form of guttapercha is trans-1,4-polyisoprene. (Isoprene is 2-methylbutadiene.) Although the synthetic type is preferred because of higher purity and predictability, both types of guttapercha can provide the following advantages: guttapercha (1) binds the ingredients of a dental composition, thereby making such a composition workable and ensuring that such a composition will have a consistent ratio of ingredients; (2) improves thermoplasticity, flexibility, compressibility and low permeability of a dental composition; and (3) remains inert to dental and periapical tissue.

The present invention combines the desirable features of calcium hydroxide and guttapercha into a single dental root canal filling composition. This combination does, however, have certain shortcomings which can be remedied by addition of further components to the composition. These shortcomings include radio-transparency and lack of rigidity. The radio-transparency is an inherent characteristic of calcium hydroxide and guttapercha, and is best countered by addition of zinc oxide or barium sulfate. The lack of rigidity in the combination of calcium hydroxide and guttapercha stems from the low density of calcium hydroxide and the consequent necessity for adding a large volume of guttapercha in order to ensure adequate binding. Lack of rigidity in the combination is preferably avoided by addition of these same radio-opaque components indicated above, i.e., zinc oxide or barium sulfate, or by addition other chemicals, such as aluminum oxide and kaolin (hydrated aluminum silicate).

Further, coloring of known type may be added to the composition to aid in recognition of size by the end user. Specifically, when the composition is used to form points, the points are manufactured to different, predetermined calibers, with each caliber having a specified color, per international standard. In this way, confusion as to the size of a particular point is avoided.

Several sample compositions are represented in the following Table:

TABLE

| SUBSTANCE | EXAMPLES | | | |
|---|---|---|---|---|
| | 1 | 2 | 3 | 4 |
| Guttapercha | 27 | 25 | 30 | 20 |
| Calcium Hydroxide | 33 | 30 | 35 | 10 |
| Zinc Oxide | 20 | 10 | 10 | 55 |
| Aluminum Oxide | 0 | 5 | 5 | 0 |
| Barium Sulfate | 20 | 20 | 20 | 15 |
| Kaolin | 0 | 10 | 0 | 0 |
| TOTAL | 100 | 100 | 100 | 100 |

Note: Data is provided in terms of weight percent.

As can be seen from the table, calcium hydroxide present in proportions of about ten (Ex. 4) to about thirty-five (Ex. 3) percent by weight is preferred. Likewise, guttapercha is preferably provided in proportions of about twenty (Ex. 4) to about thirty (Ex. 3) percent by weight. When calcium hydroxide is used in proportions of between thirty and thirty-five percent, guttapercha is preferably present in proportions of between twenty-five and thirty percent, as seen in Examples 1–3. When calcium hydroxide is provided in an amount of about ten percent by weight, guttapercha is preferably provided in an amount of about twenty percent by weight. Most preferably, calcium hydroxide, guttapercha, zinc oxide, barium sulfate, and optionally aluminum sulfate and kaolin, are provided in amounts substantially as exemplified.

In each of the examples listed in the Table, coloring can replace any of the components so as to comprise as much as one percent by weight. Testing of the above examples revealed that each demonstrated the radio-opacity and rigidity above the minimum dictated by the international specification ISO/DIS 6877.2. Moreover, the compositions described by each example showed release of calcium hydroxide, when immersed in water, even after two years of storage without special protective packaging. This result shows that the compositions effectively release calcium hydroxide.

Points made from the composition of the present invention fall into two categories, principal points and accessory points. Principal points are manufactured to standard dimensions and are used to fill most of a root canal. Suitable instruments, such as files and enlargers, are used to prepare root canals for insertion of the principal points. Accessory points are used in so-called "lateral condensation procedures" in which the accessory points are used to fill voids between a principal point and walls of a root canal. Such voids invariably result when the principal point is not exactly the same shape as the root canal, a common occurrence. In order to be used as described, both categories of points must be flexible yet rigid, thermoplastic, compressible, and capable of being cut with a heated knife or other heated instrument.

Manufacture of both types of points is accomplished by a method including the following steps: The ingredients are mixed in a cylinder mixer and the resulting paste is laminated and wiredrawn in a cylinder wiredrawer. Sheets of the composition are thus formed. These sheets are transversely cut into narrow bands or filaments of widths that depend on the caliber of the points to be formed. The filaments separated from these bands so cut are plasticized by known means and rolled over a planar surface using a plastic plate. In this way, the composition is rolled into a length, thickness, and conical shape of the desired points. Alternately, the points can be formed by heating the aforementioned paste and injecting it into molds of the desired shape, thereby forming the points.

It is to be understood that the present invention is not limited to the embodiments described above, but encompasses any and all embodiments within the scope of the following claims.

I claim:

1. A dental composition comprising:
   calcium hydroxide;
   guttapercha;
   a radio-opaque substance; and
   a substance which adds rigidity to the composition;
   wherein said calcium hydroxide is present in proportions of about ten to thirty five percent by weight; and
   said guttapercha is present in proportions of about twenty to thirty percent by weight.

2. The dental composition according to claim 1, wherein said radio-opaque substance is selected from the group consisting of barium sulfate and zinc oxide.

3. The dental composition according to claim 1, wherein said substance which adds rigidity to the composition is selected from the group consisting of barium sulfate, aluminum oxide, kaolin and zinc oxide.

4. The dental composition according to claim 1, wherein:
   said guttapercha is provided in an amount of about twenty-seven percent by weight;
   said calcium hydroxide is provided in an amount of about thirty-three percent, by weight;
   said radio-opaque substance is barium sulfate in an amount of about twenty percent, by weight;
   said substance which adds rigidity to the composition is zinc oxide in an amount of about twenty percent, by weight.

5. The dental composition according to claim 1, wherein:
   said guttapercha is provided in an amount of about twenty-five percent by weight;
   said calcium hydroxide is provided in an amount of about thirty percent, by weight;
   said radio-opaque substance is zinc oxide in an amount of about ten percent, by weight, and barium sulfate in an amount of about twenty percent by weight;
   said substance which adds rigidity to the composition is kaolin in an amount of about ten percent, by weight, and aluminum oxide in an amount of about five percent, by weight.

6. The dental composition according to claim 1, wherein:
   said guttapercha is provided in an amount of about thirty percent by weight;
   said calcium hydroxide is provided in an amount of about thirty-five percent by weight;
   said radio-opaque substance is barium sulfate in an amount of about twenty percent by weight and zinc oxide in an amount of about ten percent by weight; and
   said substance which adds rigidity to the composition is aluminum oxide in about an amount of five percent by weight.

7. The dental composition according to claim 1, wherein:
   said guttapercha is provided in an amount of about twenty percent by weight;
   said calcium hydroxide is provided in an amount of about ten percent by weight;
   said radio-opaque substance is barium sulfate in an amount of about fifteen percent by weight;
   said substance which adds rigidity to the composition is zinc oxide in an amount of about fifty-five percent by weight.

8. The dental composition according to claim 1, wherein:
   said calcium hydroxide is present in proportions of between thirty and thirty five percent, by weight; and
   said guttapercha is present in proportions of between twenty-five and thirty percent, by weight.

9. The dental composition according to claim 8, further including:
   about twenty percent barium sulfate, by weight; and
   about twenty percent zinc oxide, by weight.

10. The dental composition according to claim 8, further including:
    about twenty percent barium sulfate, by weight; and
    about ten percent zinc oxide, by weight.

11. The dental composition according to claim 10, further including about five percent aluminum oxide, by weight.

12. The dental composition according to claim 1, wherein:
    said calcium hydroxide is provided in an amount of about ten percent, by weight; and
    said guttapercha is provided in an amount of about twenty percent, by weight.

13. The dental composition according to claim 12, further including:
    about fifteen percent barium sulfate, by weight; and
    about fifty-five percent zinc oxide, by weight.

* * * * *